(12) United States Patent
Bright et al.

(10) Patent No.: US 6,492,182 B1
(45) Date of Patent: Dec. 10, 2002

(54) MICROSENSOR ARRAYS AND METHOD OF USING SAME FOR DETECTING ANALYTES

(75) Inventors: Frank V. Bright, Williamsville, NY (US); Brett R. Wenner, Lexington, KY (US); Meagan A. Doody, Guilderland; Gary A. Baker, Buffalo, both of NY (US)

(73) Assignee: The Research Foundation of State University of New York, Amherst, NY (US)

( * ) Notice: Subject to any disclaimer, the term of this patent is extended or adjusted under 35 U.S.C. 154(b) by 34 days.

(21) Appl. No.: 09/628,209

(22) Filed: Jul. 28, 2000

Related U.S. Application Data

(60) Provisional application No. 60/145,856, filed on Jul. 28, 1999.

(51) Int. Cl.[7] .............................................. G01N 21/76
(52) U.S. Cl. ........................ 436/172; 436/164; 436/165; 436/527; 422/55; 422/82.05; 422/82.08
(58) Field of Search .............................. 422/55, 56, 58, 422/82.05–82.11; 436/164, 165, 168, 169, 172, 173, 527; 250/250

(56) References Cited

U.S. PATENT DOCUMENTS

| | | | | |
|---|---|---|---|---|
| 4,737,464 A | * | 4/1988 | McConnell et al. | 436/43 |
| 4,789,214 A | * | 12/1988 | Vilhelmsson et al. | 385/147 |
| 5,200,334 A | * | 4/1993 | Dunn et al. | 435/182 |
| 5,281,395 A | | 1/1994 | Markart et al. | |
| 5,320,814 A | | 6/1994 | Walt et al. | 422/82.07 |
| 5,512,490 A | | 4/1996 | Walt et al. | 436/171 |
| 5,894,351 A | * | 4/1999 | Colvin | 356/417 |

* cited by examiner

Primary Examiner—Jill Warden
Assistant Examiner—Yelena Gakh
(74) Attorney, Agent, or Firm—Hodgson Russ LLP

(57) ABSTRACT

A device for detection of one or more analytes in a sample is disclosed. The device can simultaneously detect and quantitate multiple analytes in a sample. The device comprises an eletromagnetic radiation generator having one or more chemical sensors thereon. The chemical sensor interacts with or reacts with specific analytes in a sample. The presence of an analyte is detected by a comparison of the spectroscopic properties of the chemical sensor in the absence and presence of the analyte. A method is also disclosed for the detection and quantitation of analytes using the device of the present invention. In addition, a method of making the device of the present invention is also disclosed.

13 Claims, 17 Drawing Sheets

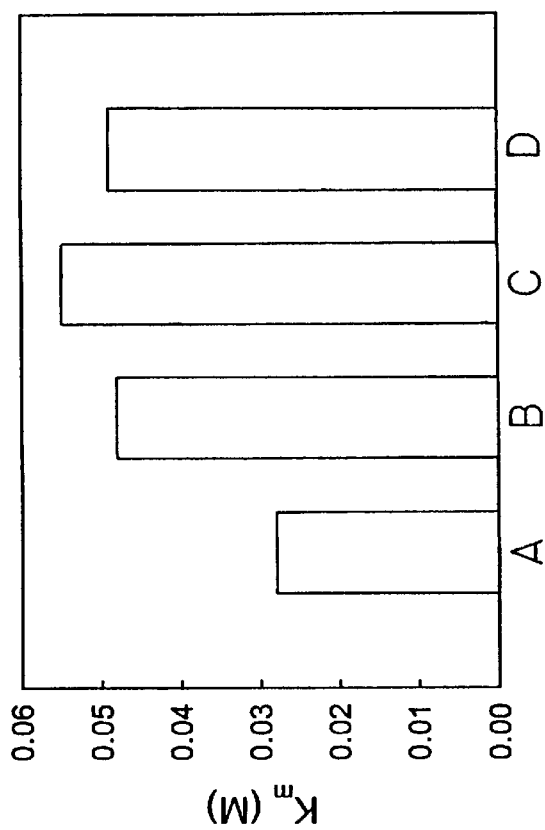
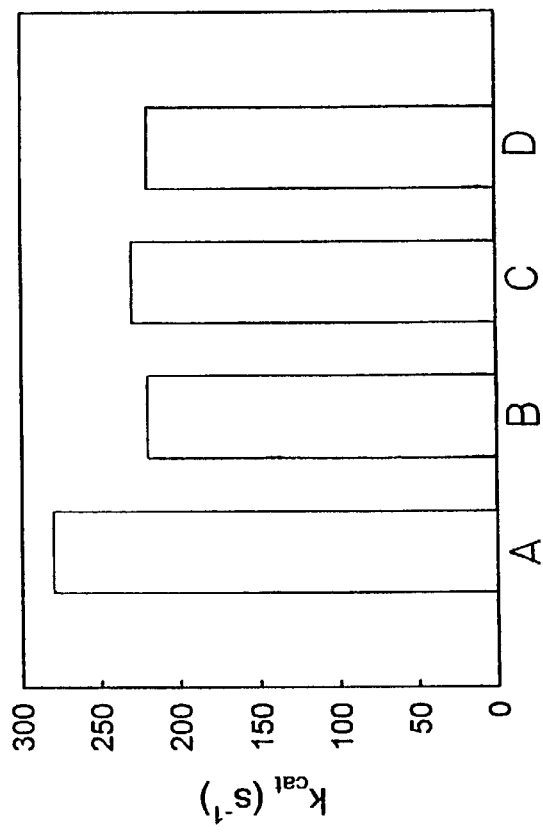
FIG. 12A
FIG. 12B

MICROSENSOR ARRAYS AND METHOD OF USING SAME FOR DETECTING ANALYTES

This application claims the priority of U.S. provisional application Ser. No. 60/145,856 filed on Jul. 28, 1999, the disclosure of which is incorporated herein by reference.

This invention was made with Government support under Grant Number N00014-96-1-0501 awarded by the Department of the Navy, and under Grant Number CHE-9626636 awarded by the National Science Foundation. The Government has certain rights in the invention.

BACKGROUND OF THE INVENTION

1. Field of the Invention

The present invention relates to the field of optical chemical detection of analytes. More particularly, the present invention provides a device wherein the electromagnetic radiation generator provides a substrate for chemical sensors, and wherein the spectroscopic properties of the chemical sensor are modified upon contacting an analyte. The present invention also provides a method for the selective and simultaneous detection and quantitation of analytes, and a method of making the device.

2. Description of the Related Art

Chemical sensors are widely used in clinical diagnosis and biomedical research to selectively detect the presence of a particular analyte or ensemble of analytes, or to measure other characteristics of samples, such as pH. These measurements are based on the principle that interaction of a chemical sensor with an analyte within a sample results in modification of spectroscopic properties of the sensor to a degree that depends on the concentration of the analyte. The modification of spectroscopic properties may involve changes in the intensity, wavelength, phase, or polarization of the incident electromagnetic radiation. For example, fluorophores are molecules that absorb light at certain wavelengths and emit light of a different wavelength (generally longer). In the presence of an analyte, the optical properties of some fluorophores are altered and this forms the basis for optical detection and quantitation of analytes using fluorophores.

Many devices disclosed previously use one or more fiber optic strands having a chemical sensor or sensor element at its tip. Some devices use an array of optical fibers to detect the presence of a substance in a sample. One such array disclosed in U.S. Pat. No. 5,320,814 has two discrete optic array ends, each of which is formed of multiple end faces of the optical fibers. On one of the optic array ends is a light energy absorbing dye disposed as an uninterrupted deposit in aligned organization upon the end faces.

Another optic sensor is disclosed in U.S. Pat. No. 5,512,490 ('490). The device comprises a supporting member and an array formed of heterogeneous semi-selective thin films which function as sensing receptor units and are able to detect a variety of different analytes and ligands using spectral recognition patterns. The supporting member may be a "supporting substrate" which is a translucent or transparent article such that light energy may pass through without being substantially altered or hindered. As shown in FIG. 2 of the '490 patent, the receptor units are formed on the supporting substrate and white light from a separate excitation source, such as an arc lamp, and a dichroic mirror are used to illuminate each receptor unit. Alternatively, the supporting member may be a collection of optical fibers, each of which is coated with a polymer/dye combination on a distal tip. As shown in FIG. 23 of the '490 patent, light from a separate excitation source in combination with a dichroic mirror is introduced into the optical fibers to illuminate the polymer/dye combination.

These and other existing devices are expensive, and bulky. Furthermore, these devices require a large amount of energy to operate, in part because the excitation light source is separate from the chemical sensor/sensor element.

SUMMARY OF THE INVENTION

The present invention provides an electromagnetic radiation (ER)-based sensor device that is simple, easy to make and is compact compared to existing devices. While any ER generator may be used for the present invention, in a preferred embodiment, the ER generator is a modified LED (light emitting diode) having micro-wells on its surface. The individual micro-wells are filled with one or more chemical sensing materials so as to form a sensor array.

Thus, an object of the present invention is to provide an ER-based sensing device that is compact and energy efficient for detecting the presence of one or more analytes in samples.

Another object of the present invention is to provide an ER-based sensing device for the simultaneous detection and quantitation of one or more analytes in a sample.

Another object of the present invention is to provide a method for detecting the presence of one or more analytes in a sample.

Another object of the present invention is to provide a method for detecting and simultaneously quantitating one or more analytes in a sample Yet another object of the present invention is to provide a method of making an ER sensor and sensor array for the detection and quantitation of one or more analytes in a sample.

A detecting device according to the present invention comprises an ER generating substrate having a chemical sensor for interacting selectively with a particular analyte in a sample. In the absence of the analyte, the chemical sensor displays certain baseline spectroscopic properties characteristic of the sensor. However, when the analyte is present in the sample, the spectroscopic properties of the chemical sensor are modified. Detection and quantitation of the analyte are based on a comparison of the modified properties and the baseline properties and the use of standard calibration methods that are well known to those skilled in the art of analytical chemistry.

The present invention also includes a method of making the detecting device. In the method of making the device according to the present invention, micro-wells are formed on an ER substrate and a chemical sensor and/or sensor element is placed therein in a suitable holding material.

BRIEF DESCRIPTION OF THE DRAWINGS

FIGS. 12a and 12b show plots of the activity of the chemical sensor, Glucose oxidase (Gox) for the detection of glucose. Activity is shown in the form of $K_m(M)$ in FIG. 12a and as $k_{cat}(s^{-1})$ in FIG. 12b for GOx's behavior in the presence of its substrate, glucose, when it is dissolved in buffer (A)—(from *J. Biol. Chem.* 1967, 242, 994 and *Biochemistry* 1971, 10, 4624) or sequestered within a tetramethylorthosilane (TMOS) derived xerogel glass (B)—(*Chem. Mater*. 1992, 4, 1615) or when GOx is held within a micro-well that uses a TMOS-derived xerogel glass as the holding agent as a function of storage time within the xerogel-filled micro-well(C)—1 month of storage at ambient conditions; (D)—8 months of storage at ambient conditions).

DETAILED DESCRIPTION OF THE PREFERRED EMBODIMENTS

Figure 2:
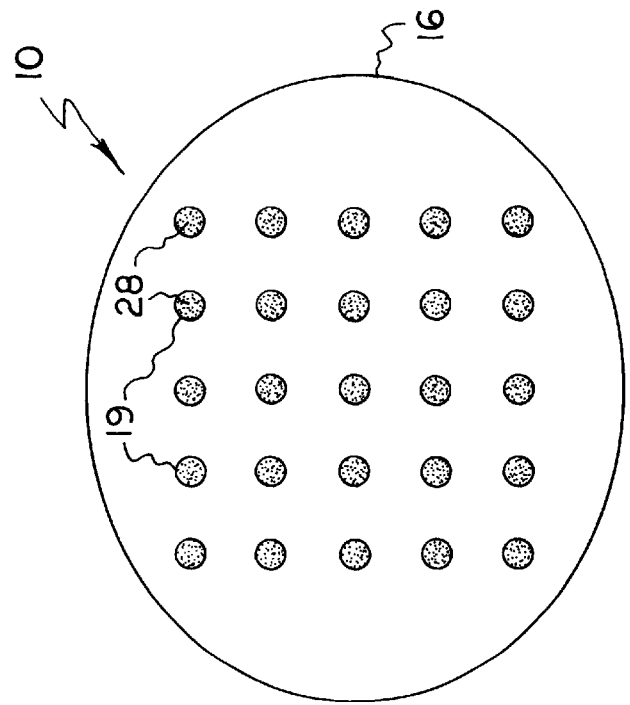
FIGS. 1 and 2 are schematic representations of a side view and a top view respectively of the detecting is device according to the present invention.

The term "chemical sensor" or "chemical sensors" as used herein means a molecule or molecules that detect(s) the presence of an analyte. The chemical sensor comprises a sensor element whose optical properties are modified in the presence of an analyte. The properties of the sensor element may be directly modified upon its interaction with the analyte. Alternatively, the sensor element may be attached to a molecule having a specific affinity for the analyte, in which case, the optical properties of the sensor element are modified upon the interaction of the affinity molecule with the analyte. Thus, by the term "spectroscopic properties of the chemical sensor" or "chemical sensor's spectroscopic properties" is meant the spectroscopic properties of the sensor element and vice versa. These properties may be optical in nature when the emitted electromagnetic radiation is within the visible spectrum i.e., between about 400 nm to about 800 nm. As an example if the chemical sensor is a fluorescein tagged antibody, the sensor element is fluorescein and the affinity molecule is the antibody. In another example, where the chemical sensor is a luminescent ruthenium dye ([Ru (dpp)$_3$]$^{2+}$), the sensor element and the chemical sensor are the same.

The present invention provides a compact and energy efficient ER sensor array. The device can also be used for the simultaneous detection and quantification of one or more analytes in a sample. The device comprises an ER generator having one or more micro-wells or zones for placement of chemical sensors. The ER generated by the generator is such that at least some of it can be absorbed by a phosphore, fluorophore, and/or chromophore of the chemical sensor. To be absorbed by the luminophore (fluorophore or phosphore) or chromophore requires that the wavelength range output from the generator overlap at least partially with one or more allowed electronic transitions within the chemical sensor or sensor element. Typically the electromagnetic radiation capable of exciting and/or populating upper electronic transitions in a substance fall within a wavelength region of 200 nm to 900 nm and thus includes, ultraviolet, visible and infrared portions of the electromagnetic spectrum.

A unique feature of the device is the placement of chemical sensor directly on the ER generator in an array or pattern. This eliminates the need for optical fibers to carry the signal from the ER generator to the chemical sensor, it improves the efficiency of delivery of electromagnetic radiation from the generator to the chemical sensor, it minimizes alignment problems, and it lowers the necessary fluence from the generator which leads to the use of smaller and lower power (e.g., battery operated) generators.

The ER generator can be any device that generates electromagnetic radiation of a wavelength that will cause electronic transitions in a chemical sensor such as light emitting diodes and diode lasers. In a preferred embodiment, the electromagnetic radiation generator is light emitting diode (LED).

The chemical sensor can be placed directly on the ER generator or it can be placed within micro-wells created A on the surface of the generator. The number, size, and shape of the micro-wells on an ER generator can vary. While any ratio of micro-wells to non micro-well area is suitable, a ratio of 1:4 generally ensures that individual wells are reasonably well separated from one another. For example, on an LED of 5 mm diameter, having 10 μm diameter wells, with a 1:4 ratio of micro-wells to non-micro-well area, it is estimated that 62,000 micro-wells can be formed. Each micro-well may contain a different chemical sensor so that the same LED may be used for the simultaneous detection and quantitation of multiple analytes.

To fill the micro-wells with the chemical sensor, a filling or holding material is used. Any material known to those skilled in the art for holding, immobilizing, entrapping, and/or sequestering chemical sensors, can be used. These materials include, but are not limited to, sol-gel derived materials, acrylamide gels, small particle beads and surface-immobilized species. One commonly used holding material is a sol-gel-derived glass. A sol-gel-derived glass is a porous glass formed by the condensation and polycondensation of one or more metal or semi-metal alkoxide mixtures. Sol-gel-derived glasses provide a convenient means to sequester sensors, and/or sensing agents, because they prevent leaching from the holding material, and the glasses themselves are porous, thereby allowing analytes to penetrate into the glass, and react with the chemical sensors. Glasses with surface areas of up to several hundred square meters per gram and narrow pore diameters (0.5 to 500 nm)are readily prepared using sol-gel methods well known to those skilled in the art of sol-gel processing chemistry. A detailed discussion of sol-gel chemistry can be found in Reisfeld et al., 1992, *Chemistry, Spectroscopy and Application of Sol-Gel glasses*, Springer-Verlag, Berlin; Brinker et al., 1989, *Sol-Gel Science*, Academic Press, New York; Dave et al., 1994, *Anal. Chem.* 66:1120A, 1121A.

It is preferred that the mean pore diameter be less than the mean wavelength of electromagnetic radiation from the generator, but deviation leads only to a predictable decrease in performance. The sol-gel-derived glass useful in the present invention is preferably transparent or translucent for wavelengths of from about 300 nm to about 900 nm. Translucent materials preferably have a transmittance of 50% or greater.

Chemical sensors may simply be added to the sol-gel-derived glass holding material once the sol-gel-derived glass is placed or located or formed in the micro-wells, or they may be doped into the sol-gel processing solution (precursor to the glass and/or xerogel) before it is filled into the micro-wells. A property that makes sol-gel-derived glass useful for the present invention is that molecules sequestered within the glass may interact with diffusible analytes or components in an adjacent liquid or gas phase within the glass pore space. In addition to sol-gel-derived glass, other organic or inorganic polymers and mixtures thereof that can be easily filled into the micro-wells and remain within the wells, can also be used as holding materials.

Chemical sensors or sensor elements that are useful for the present invention include materials whose spectroscopic properties are modified due to interaction with specific analytes. The modification of spectroscopic properties may include a change in wavelength, intensity, phase, and/or polarization of the incident electromagnetic radiation.

Materials that cause a change in the wavelength of incident (exciting) ER are referred to as fluorophores or phosphores and typically absorb ER of a particular wavelength and emit ER of a different wavelength. The absorption and emission spectra are characteristic for each fluorophore or phosphore. Materials that absorb electromagnetic radiation and do not fluoresce, generally convert any excess energy produced as a result of photoexcitation into heat energy or kinetic energy and are referred to as chromophores. Many dyes are known in the art that absorb electromagnetic radiation of a specific wavelength.

The detection of the transmitted or emitted electromagnetic radiation from the chemical sensor may be carried out by collecting the electromagnetic radiation from each individual micro-well with an objective, passing it through a filter system and ultimately communicated to a solid state array detector, such as a charge coupled device (CCD).

The following examples are presented for illustrative purposes and are not to be construed as limiting.

Figure 1:
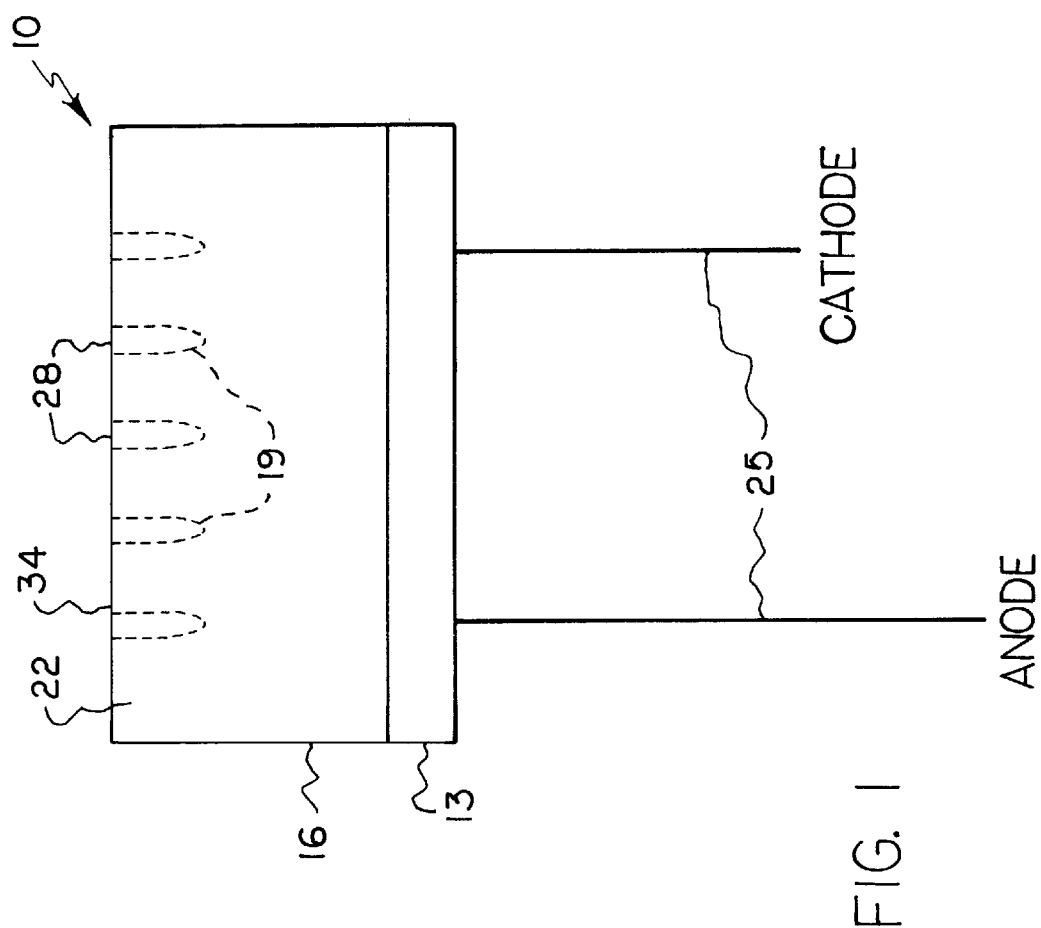

FIGS. 1 and 2 illustrate an LED having micro-wells thereon. LEDs are typically covered with a protective coating. Thus, the detecting device 10 according to the present invention, includes an ER generator 13 in contact with the protective layer 16. The protective layer 16 is a substance which is transparent or translucent to electromagnetic radiation generated by the substrate 13. Preferably, the transmittance is 50% or greater. The protective layer 16 has one or more micro-wells 19 formed in a distal end 22 of the protective layer 16. The micro-wells 19 preferably extend into the protective layer 16, but not through the protective layer 16 to the point that they contact the actual LED p-n junction. The LED generates electromagnetic radiation when an electric potential is applied via the conductors 25. Any commercially available LED can be used for this invention. The primary consideration is that the electromagnetic radiation emitted by the LED be at least partially absorbed by the chromophore(s), fluorophore(s), and/or phosphore(s) that comprise the sensor(s).

Within each discrete micro-well 19 is a combination 28 of a holding material and a chemical sensor, which is capable of selectively interacting with the analyte to be detected and quantified. When the LED generates electromagnetic radiation, the chemical sensor displays a characteristic spectroscopic property. For example, the chemical sensor may emit light of one wavelength in the absence of the analyte. When the chemical sensor interacts with the analyte, its optical properties are modified, and it may emit light of a second wavelength. In some cases, an analyte may interact with a chemical sensor to change its intensity or polarization of fluorescence. The change in the intensity or polarization may involve an increase or decrease. It should be noted that the sensor element of the chemical sensor may itself interact with the analyte or alternatively, the sensor element may be attached to another molecule or fragment of a molecule that interacts selectively with the analyte.

The chemical sensor is held within a micro-well 19 by a transparent or translucent holding material, preferably with a transmittance of 50% or greater, which may be any of the organic or inorganic polymers, or mixtures thereof, which are well known in the art for sequestering chemical sensors. Preferably, the holding material is a sol-gel-derived glass which forms a porous xerogel or aerogel upon setting in the well 19. One such holding material suitable for use in the present invention is a sol-gel-derived glass comprised of TMOS.

Figure 4:
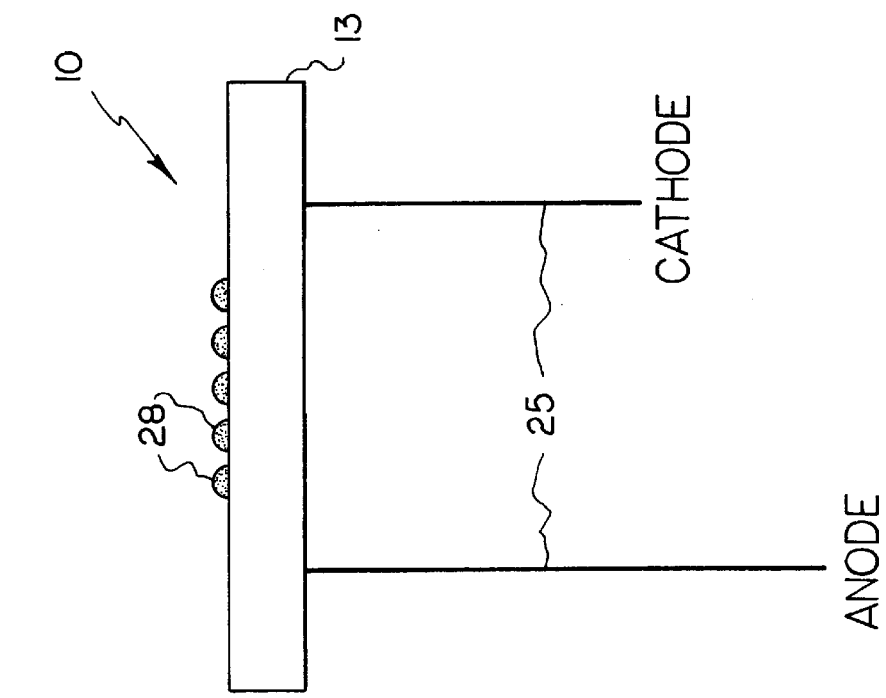
FIGS. 3 and 4 are schematic representations of side views of two embodiments of the detecting device according to the present invention.
Figure 3:
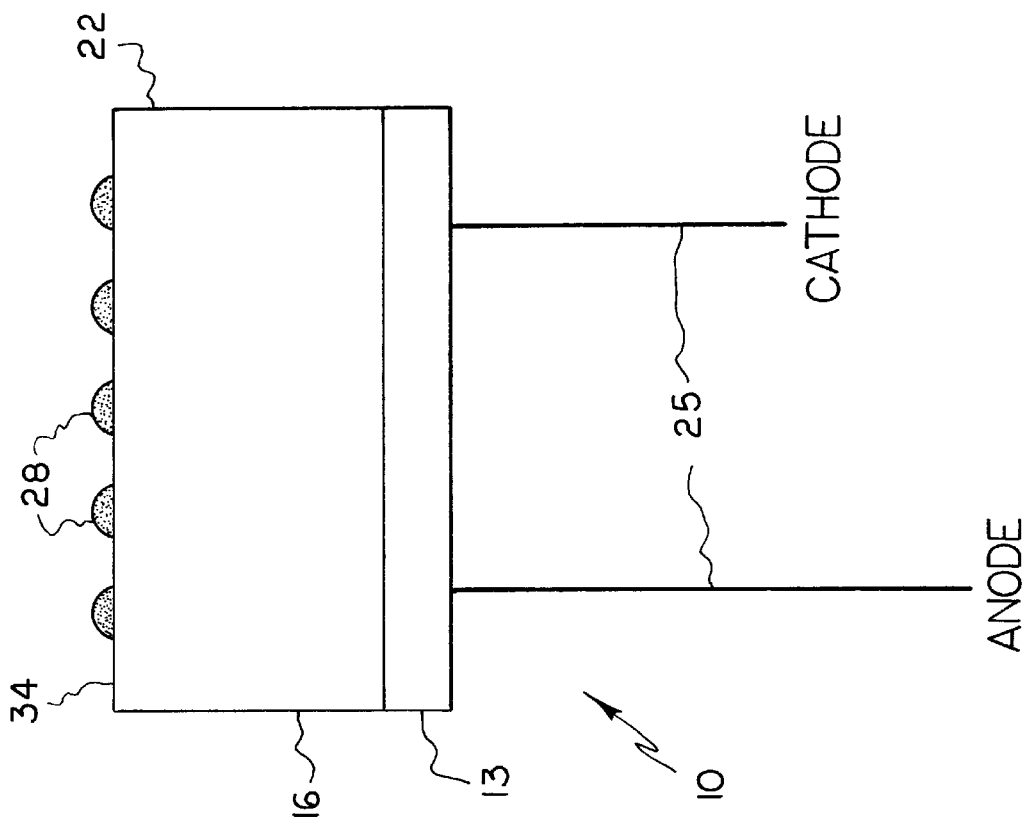

FIGS. 3 and 4 depict another embodiment of the present invention in which no well is used. In the embodiment shown in FIG. 3, the chemical sensor is placed directly on a substantially planar surface 34 of the protective layer 16. The chemical sensor may be placed on the planar surface 34 by using a micropipette or microinjector to deliver the sensor and its holding material on the planar surface 34. Alternatively, the chemical sensor may be placed directly on the substrate 13, as shown in FIG. 4, in the absence of a protective layer. The chemical sensor may be fixedly attached to the substantially planar surface 34 of the protective layer 16 by mixing it with the sol-gel-processing solution described above, and then placing the combination 28 on the planar surface 34, where the combination is allowed to set.

The chemical sensors of the present invention comprise a sensor element, whose optical properties are modified in the presence of an analyte. Sensor elements that can be used for the present invention include electromagnetic radiation absorbing and electromagnetic radiation emitting inorganic or organic dyes (either natural, synthetic, or combinations thereof). Such dyes include phosphores, fluorophores, and chromophores. Many luminescent and chromogenic molecules are well known to those skilled in the art. Examples of such materials are disclosed in U.S. Pat. No. 5,250,264. Other sources of useful chemical sensors or sensor elements include the Handbook of Fluorescent Probes and Research Chemicals, 6th ed., authored by Richard P. Haugland and published by Molecular Probes, Inc. of Eugene, Oreg. As discussed above, some of the chemical sensors absorb light emitted from the LED in the presence of an analyte to a degree that depends on the analyte concentration, while others luminescence to a degree that depends on the analyte concentration in the presence of the analyte to be detected and/or quantified. Also as mentioned above, the sensor element may directly detect the analyte or may indirectly detect the analyte through an affinity molecule. Such affinity molecules will have substantial affinity for the analyte and include inorganic or organic ligands; inorganic or organic chelators; proteins, including antibodies, enzymes and binding proteins; and nucleic acids. These molecules may be natural or synthetic.

The types of analytes that may be detected include both liquid and gaseous materials. These include $CO_2$, $O_2$, pesticides, drugs, herbicides, anions, cations, antigens, oligonucleotides, and haptens. Further, the present invention can indicate the pH of a sample. In addition, chemical sensors are available and can be used in the present invention to detect the presence of organic molecules such as polycyclic aromatic hydrocarbons, glucose, cholesterol, amino acids, peptides, DNA and RNA. There are many more substances which can be detected, and the foregoing list is not to be considered exhaustive, but instead is merely representative.

Figure 5:
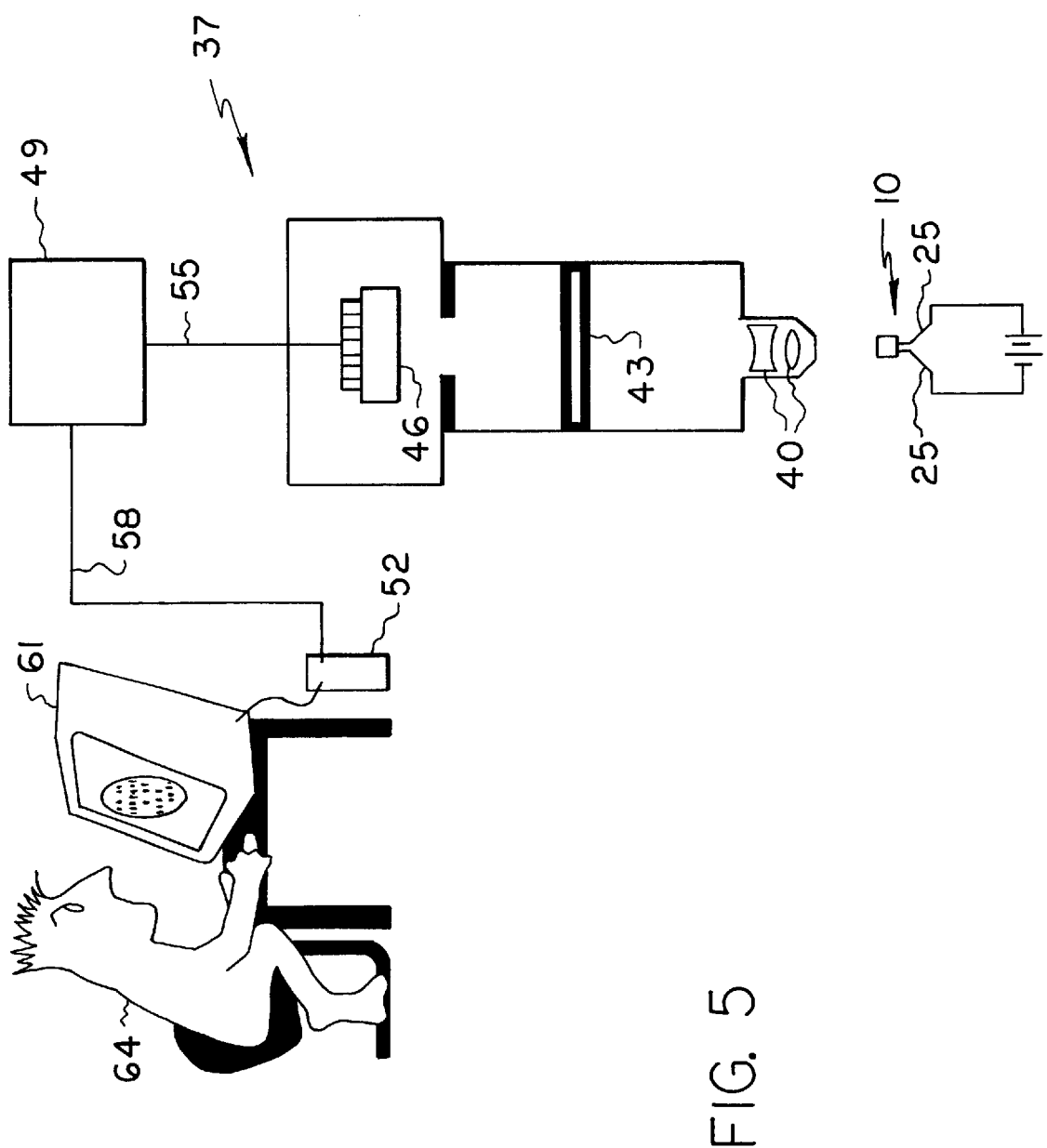
FIG. 5 is a schematic representation of the detecting device according to the present invention in combination with a receiving and interpreting system.

The electromagnetic radiation emitted by the chemical sensor may be detected by any suitable method known in the art. A general configuration is illustrated in FIG. 5, which shows a detecting device 10 according to the present invention in combination with a receiving and interpreting system 37. The receiving and interpreting system 37 has a receiver to receive electromagnetic radiation transmitted or emitted by the chemical sensor and an interpreter to interpret the received radiation. The receiver shown in FIG. 5 includes a lens or series of lenses 40, a filter 43 and a receiving surface 46. A suitable receiver is a microscope objective. The receiver may have a camera for recording images. The interpreter includes a controller 49 and a computer 52 having software running thereon. The receiving surface 46 is connected to the controller 49 via first communication line 55. The controller 49 is connected to the computer via second line 58.

An example of a device having a series of lenses 40, is a standard inverted fluorescence microscope. An example of a microscope suitable for use in the present invention is, model number BX-FLA available from Olympus America, Inc. of Melville, N.Y.

The receiving surface 46 may be a charge coupled device, which may be part of a CCD camera. An example of a CCD camera which can be used in the present invention is model number TE/CCD-1317K manufactured by Princeton Instruments, Inc. of Trenton, N.J. An example of a controller 49 which is suitable for use in the present invention is model number ST-138 manufactured by Princeton Instruments.

A filter 43 may be placed between the substrate 13 and the receiving surface 46. The filter 43 selectively passes desired wavelengths of the electromagnetic radiation moving from the detecting device 10 toward the receiving surface 46 and blocks undesired wavelengths. An example of a filter 43 which can be used to practice the present invention is model number XF 3000-38 manufactured by Omega Optical of Brattleboro, Vt. This particular filter passes electromagnetic radiation above approximately 515 nm and strongly attenuates electromagnetic radiation below approximately 515 nm. Other filters or filter combinations are possible depending on the generator wavelength and the particulars associated with a given sensor.

Figure 6:
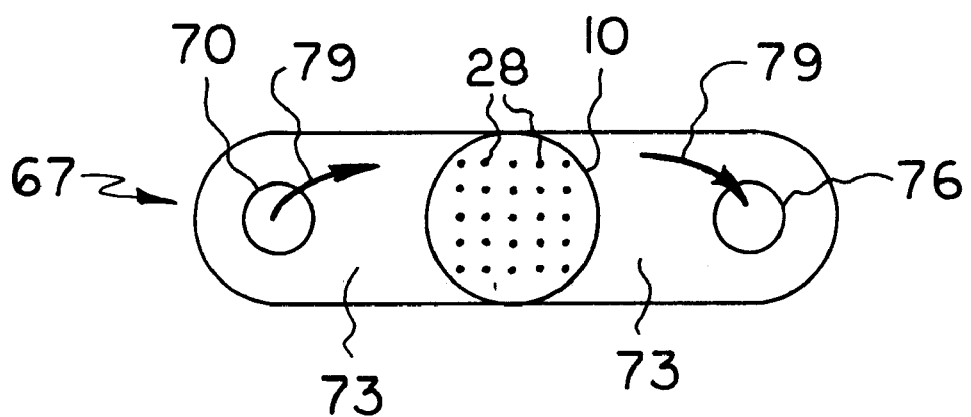
FIGS. 6 and 7 are schematic representations of a top view and a side view respectively of a detecting device according to the present invention in combination with a flow cell.
Figure 7:
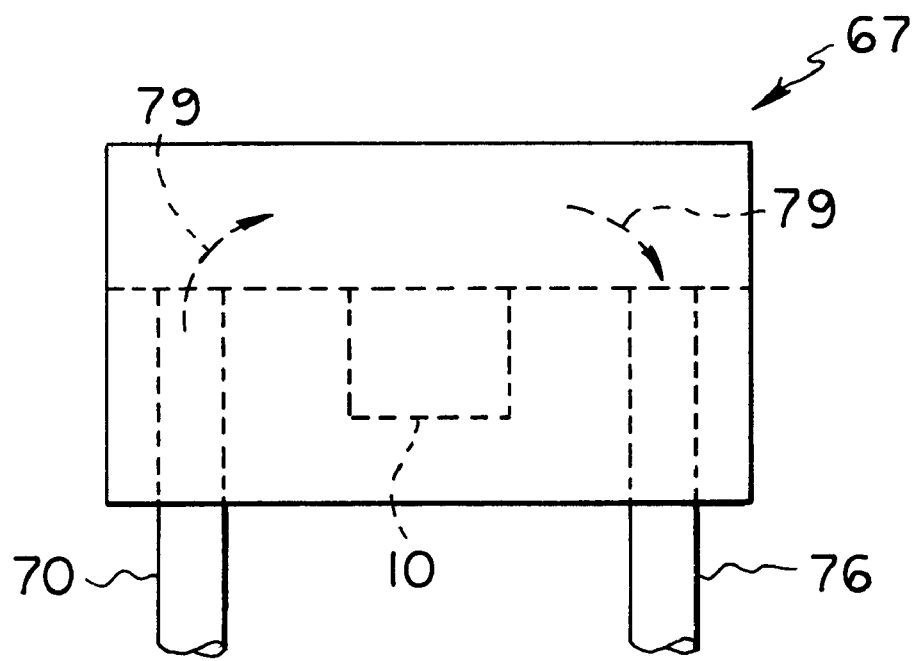

FIGS. 6 and 7 depict an embodiment of the present invention in which a detecting device 10 according to the present invention is positioned within a flow cell 67. The flow cell 67 permits continuous monitoring of a stream of sample or discretely injected plugs from multiple samples. The flow cell 67 has an inlet 70, a channel 73 and an outlet 76. A sample to be analyzed is provided at the inlet 70, flows through the channel 73 in the direction indicated by arrows 79, and finally leaves the channel 73 via the outlet 76. As the sample flows over the detecting device 10, the sample contacts and interacts with the chemical sensor(s).

It will be recognized by those skilled in the art that a flow cell 67 need not be provided to practice the present invention. The chemical sensor(s) is merely contacted with a sample to be analyzed, and then placed in the proper position to permit the receiving and interpreting system 37 to receive radiation from the chemical sensors. Consequently, in lieu of using the flow cell 67, the detecting device 10 may be dipped in a sample and then properly positioned relative to the receiving and interpreting system 37.

Figure 8A:
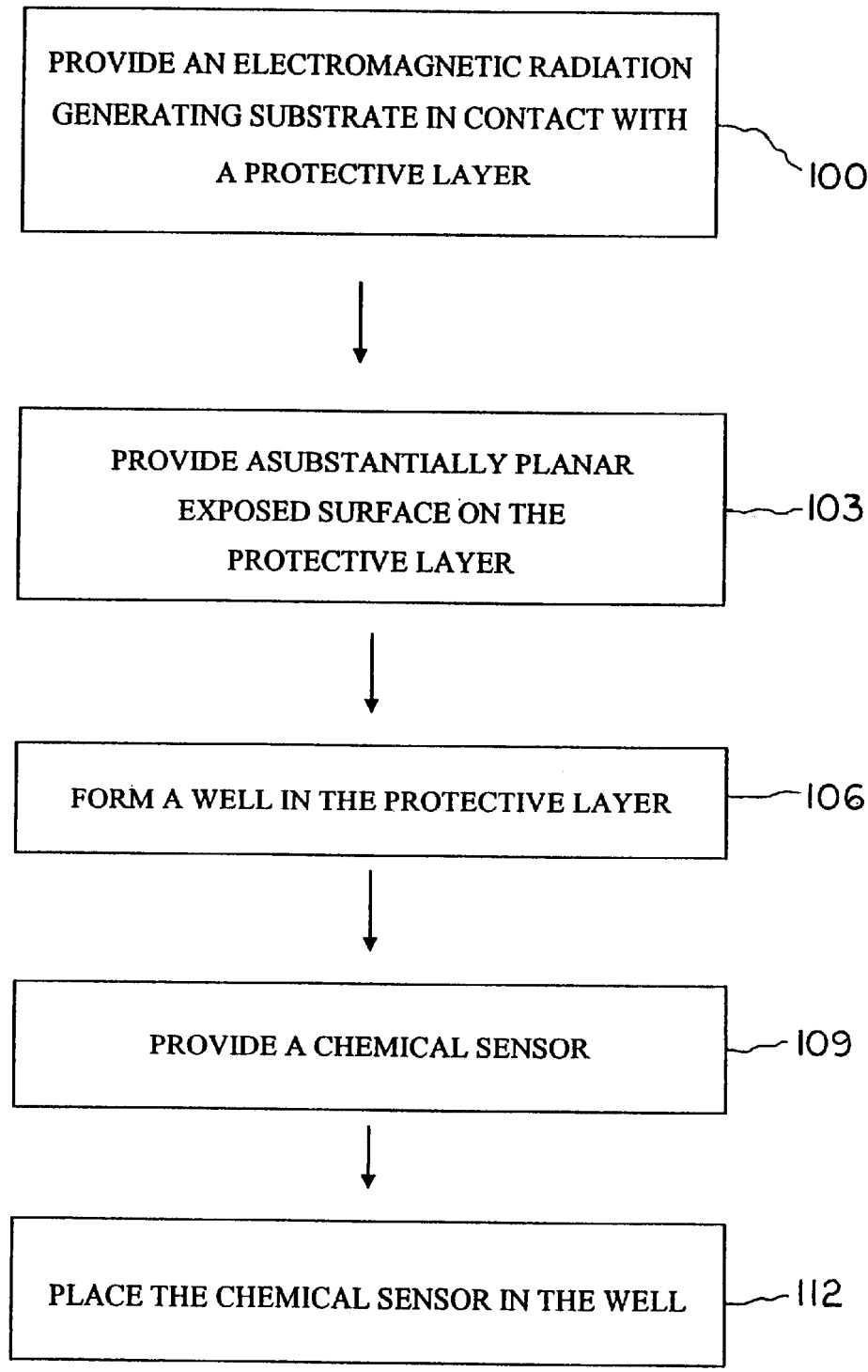
FIGS. 8a and 8b show steps of two methods for making the detecting device according to the present invention.

The device of the present invention can be made by preparing micro-wells on the surface of an ER generator. Steps for preparing a device according to the present invention are illustrated in FIG. 8a. As discussed above, a suitable ER generator is an LED (Step 100). It is preferable to have a planar surface on the LED for making the micro-wells (Step 103). Thus, if the LED has a non-planar tip, a portion of it may be removed to provide a substantially planar exposed surface. The micro-wells can be formed either on the protective layer (step 106) that is generally present on the LED or they can be formed on the LED after removal of some or all of the protective layer. The wells are preferably formed by any micromachining methodology. Examples of micromachining methods include mechanical drilling with small diameter drill bits, chemical etching/lithography, and/or laser-based drilling with a continuous wave or pulsed laser by free hand or with a predetermined pattern (Step 106). Alternatively, the protective layer may be molded to have the micro-wells as an intrinsic part of the LED, thereby alleviating the need to remove portions of the protective layer and micromachining steps to form a well. A suitable well depth is from 0.1 mm to 1 mm, but other depths are suitable for certain applications where faster response time and/or greater overall signal-to-noise is required. A micro-well can be formed by mechanically drilling into the LED to a defined depth. The depth is controlled by mechanically translating the drill and/or LED on a lathe and or drill press. The LED and drill can then be moved relative to one another, the next well is drilled, and so on until an array of microwells on the LED face is formed. A similar strategy can be used for laser-based drilling where the laser beam and/or the LED can be translated with respect to one another to effect a pattern. Here the laser beam fluence, laser illumination time on the LED face, and/or elaser beam focal point waist can all be used to precisely control the micro-well depth, well position, and well diameter. One can also use the laser-based method in concert with a template to micromachine a pattern or array of micro-wells on the face of an LED or other generator. Next, a sol-gel-processed solution is added into the micro-wells using a micro-pipette and/or a microinjector with a micromanipulator. A defined volume is added into each micro-well. The contents of each micro-well are allowed to age/cure for a defined time that depends precisely on the well depth, its diameter, and the exact composition of the holding agent phase. The chemical sensor is prepared (Step 109) and may be added to the micro-wells using a micropipette or a microinjector after the wells are filled with the sol-gel-derived glass or it can be mixed directly with the sol-gel-processing solution before filling (Step 112).

Figure 8B:
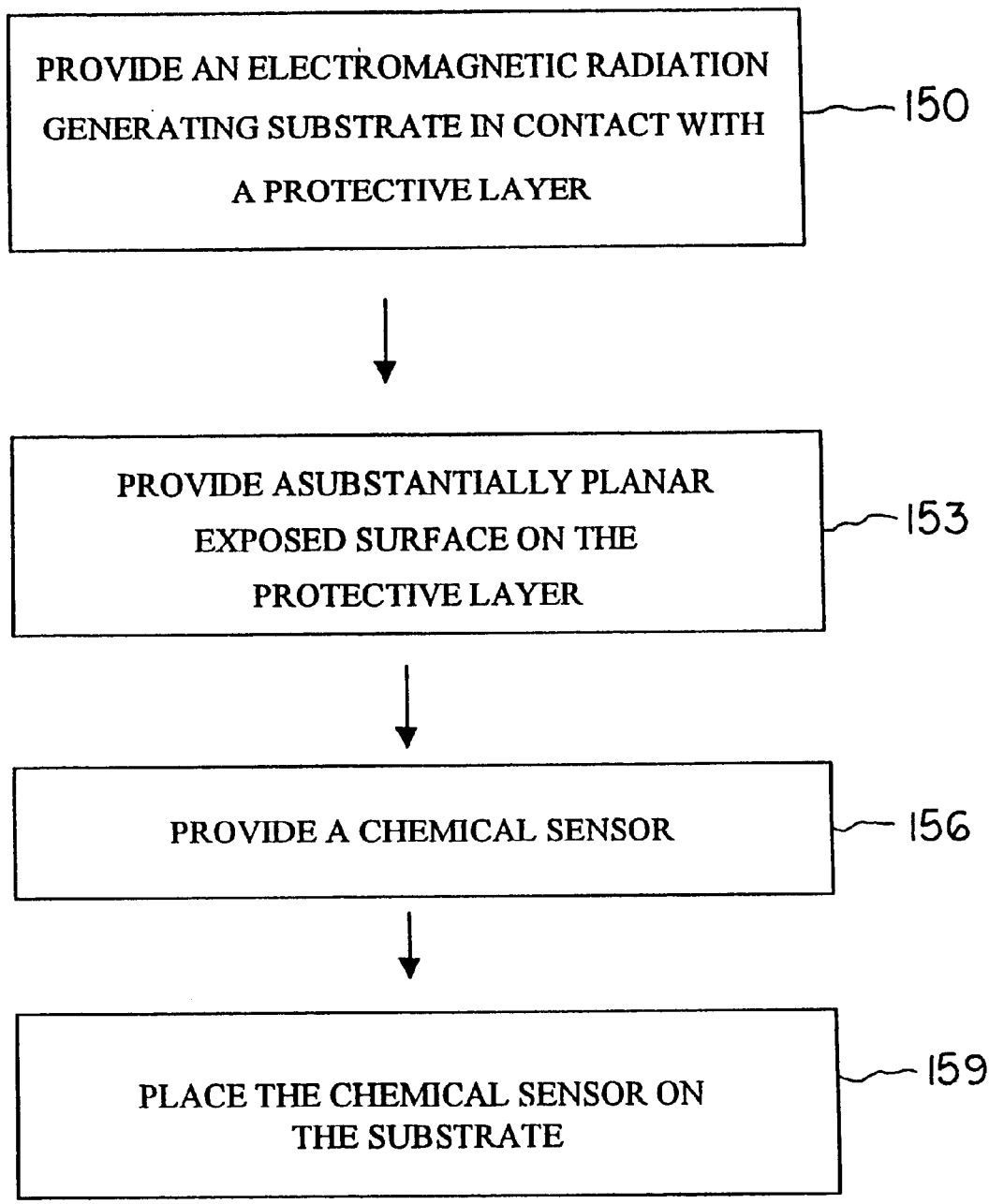

In one embodiment, the device may be prepared without creating micro-wells. Thus, the steps illustrating this embodiment are presented in FIG. 8b. A suitable ER generator is provided (with or without the protective layer) (Step 150). It is preferable to have a planar surface on the LED for deposition of the chemical sensor (Step 153). If the LED has a non-planar tip, a portion of it may be removed to provide a substantially planar exposed surface. The chemical sensor is prepared (Step 156) mixed with the sol-gel-processing solution for deposition (Step 159).

The detecting device 10 described herein and the receiving and interpreting system 37, as illustrated in FIG. 5 can be used to practice a method of the present invention. The method comprises the steps of obtaining a baseline reference of the desired spectroscopic property of the chemical sensors. For example, the fluorescence intensity or the fluorescence wavelength from an individual micro-well or array of micro-wells on the face of an LED having a chemical sensor or array of sensors may be recorded. Then the detecting device 10 is contacted with a sample containing one or more target analytes. The spectroscopic properties of the contacted chemical sensor are recorded again and compared to the baseline reference. Any detectable deviation of the spectroscopic properties from the baseline indicates the presence of the analyte. The concentration of the analyte is obtained by comparing the deviation of the spectroscopic properties from the baseline and the sample to the deviation observed from a calibrated set of known standards. Those skilled in the art will recognize that the concentration or quantity of analyte in the sample may also be obtained without determining the deviation of the spectroscopic properties from the baseline by simply comparing the spectroscopic properties of the chemical sensor in the presence of the analyte with a calibrated set of standards.

Figure 9:
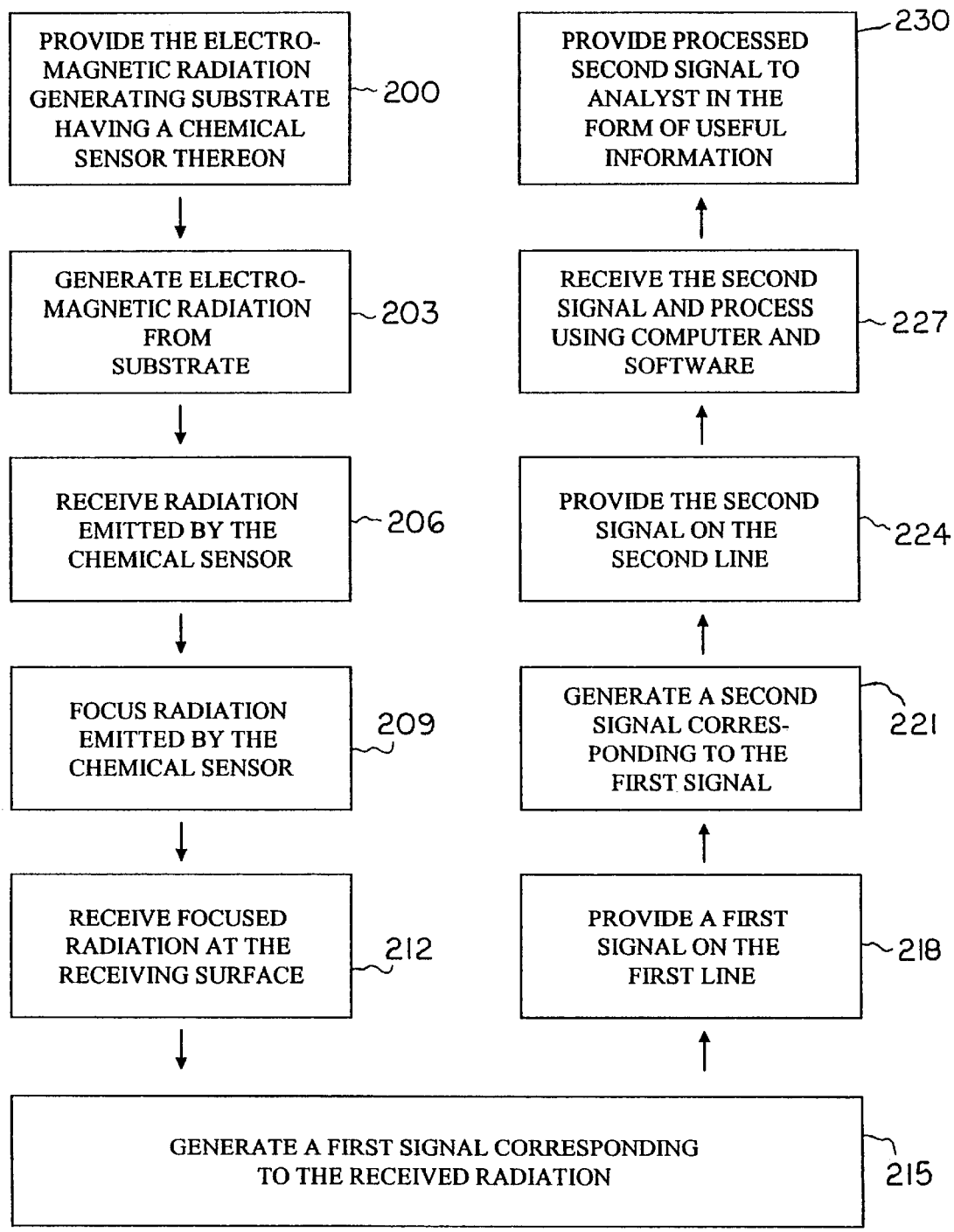
FIG. 9 shows steps of a method of detecting the presence of an analyte in a sample using an electromagnetic radiation generating substrate according to the present invention.

An illustration of the steps involved in the detection of analytes is presented in FIG. 9. The ER generating substrate is provided (Step 200). For operation, a signal is generated from the ER generating substrate which has micro-wells containing an ensemble of discrete chemical sensors (Step 203). Emitted radiation from the chemical sensors is received (Step 206), focused (Step 209) and received at the receiving surface (Step 212). The receiving surface then generates a first signal corresponding to the received radiation (Step 215). The first signal is transmitted on the first communication line 55 to the controller 49 (Step 218). The controller 49 in turn generates a second signal corresponding to the first signal (Step 221), and provides the second signal on the second communication line 58 (Step 224). The second signal is formed by the controller 49 to conform to a transmission format understandable by the computer 52 (Step 227). Then the computer 52 receives the second signal via the second communication line 58 and processes the second signal using software running on the computer 52 to provide (Step 230) a processed second signal in the form of useful information about the radiation received by the receiving surface 46 to the analyst 64.

The following specific embodiments describe the use of the present invention in the detection and quantitation of analytes.

EXAMPLE 1

This embodiment illustrates the preparation of one sol-gel composition suitable for the present invention. It should be recognized that this is a specific description of the preparation of a particular sol-gel-derived glass material. Other sol-gel-derived materials can be prepared using obvious variants of this method based on the information provide herein and by using protocols that are known in the art of sol-gel chemistry. The Ru(dpp) 32+-Doped Sol-gel-derived thin films were prepared as follows. An acid-catalyzed sol-gel-processed stock solution was prepared by mixing TMOS (15 mmole), deionized water (30 mmole), EtOH (30 mmole), and HCl (15×10−4 mmole). This solution was stirred under ambient conditions for 4 h. The mixture was then transferred into a clean glass vial. Fifty microliters of [Ru(dpp)3]2+dissolved in EtOH. The ethanolic [Ru(dpp)3]2+solutions contained approximately 100 micromoles of Ru(dpp) 32+. The solutions were allowed to stir for 1 h. The solution were transferred into microwells and allowed to age under ambient conditions for 2 days.

EXAMPLE 2

Figure 10:
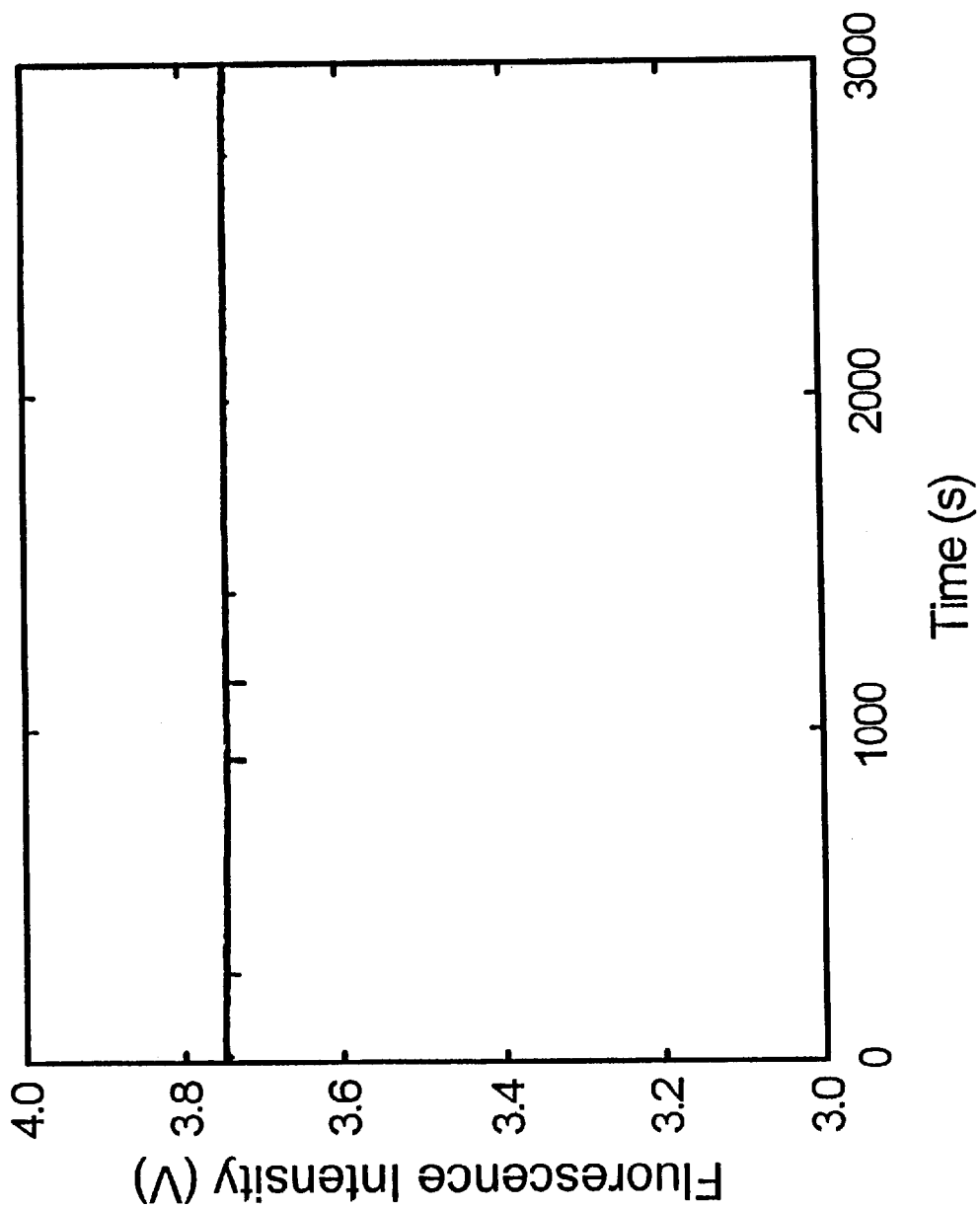
FIG. 10 shows the luminescence intensity, as a function of time, from a single micro-well located on the face of an LED according to the present invention having the chemical sensor tris(4,7-diphenyl-1,10-phenanthroline) ruthenium (II) sequestered within a holding material.

This embodiment demonstrates the stability of the chemical sensor in a holding material according to the present invention. A sol-gel-derived xerogel containing tris(4,7-diphenyl-1,10-phenanthroline) ruthenium (II) ($[Ru(dpp)_3]^{2+}$), an organometallic luminescent molecule, was prepared as described above. The dye concentration was ~25 uM. Microwells on an LED were filled by hand with a micropipette. A typical volume added into a micro-well was ~1–2 uL. Incident light of ~470 nm was produced by the LED, this light excited the $[Ru(dpp)_3]^{2+}$-doped xerogel that filled the micro-wells and the $[Ru(dpp)_3]^{2+}$ luminesced. The luminescence output from a single micro-well was monitored continuously while the sensor was operating in air. As shown in FIG. 10, the intensity of luminescence was constant over a 3000 second period under constant operation and there was no evidence of any dye photobleaching. Thus, this data demonstrates that using the method of the present invention, the chemical sensor is sufficiently stable to be used for detection and quantitation.

EXAMPLE 3

Figure 11:
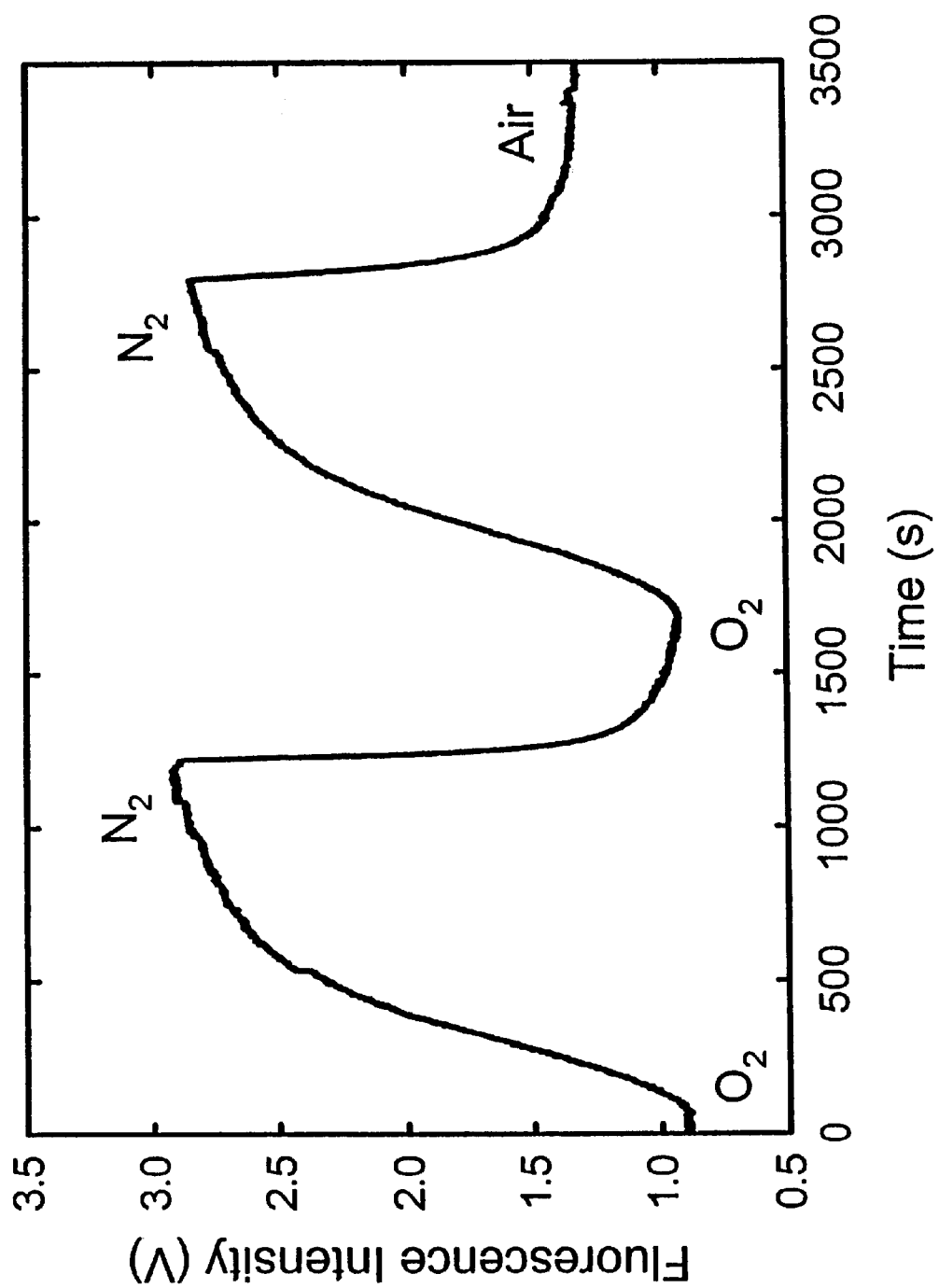
FIG. 11 shows the fluorescence intensity of electromagnetic radiation emitted by the sensor of FIG. in response to gaseous $O_2$ (a quencher),$N_2$ (a non-quencher), and air (partial quencher).

This embodiment demonstrates the reliability of the device and method of the present invention. In one illustration of this embodiment, the selectivity of a response using a chemical sensor is demonstrated. The LED from Example 1 was contacted with analytes whose effects on this chemical sensor are known. Oxygen is known to quench the luminescence of this chemical sensor while nitrogen is known not to have any effect. FIG. 11 shows the response profile upon repeated challenge of a $[Ru(dpp)_3]^{2+}$-doped xerogel-filled micro-well on an LED face when the sample stream is switched from $O_2$ (low fluorescence)to $N_2$ (higher fluorescence) to air (intermediate fluorescence). Thus, this embodiment illustrates reversibility, reproducibility, selectivity, and response time of the device and method of the present invention.

EXAMPLE 4

This embodiment demonstrates the sensor stability, for storage purposes, of a micro-well that is filled with a sol-gel-derived glass containing a chemical sensor. FIG. 12 shows a comparison of the performance of the enzyme glucose oxidase (GOx) dissolved in aqueous solution (A) or TMOS (B), or sequestered within a sol-gel-derived glass that has been stored for 1 month (C) and eight months (D). As shown in FIG. 12, GOx, sequestered within a sol-gel-derived glass within a micro-well, is reasonably stable for at least 8 months.

Figure 13:
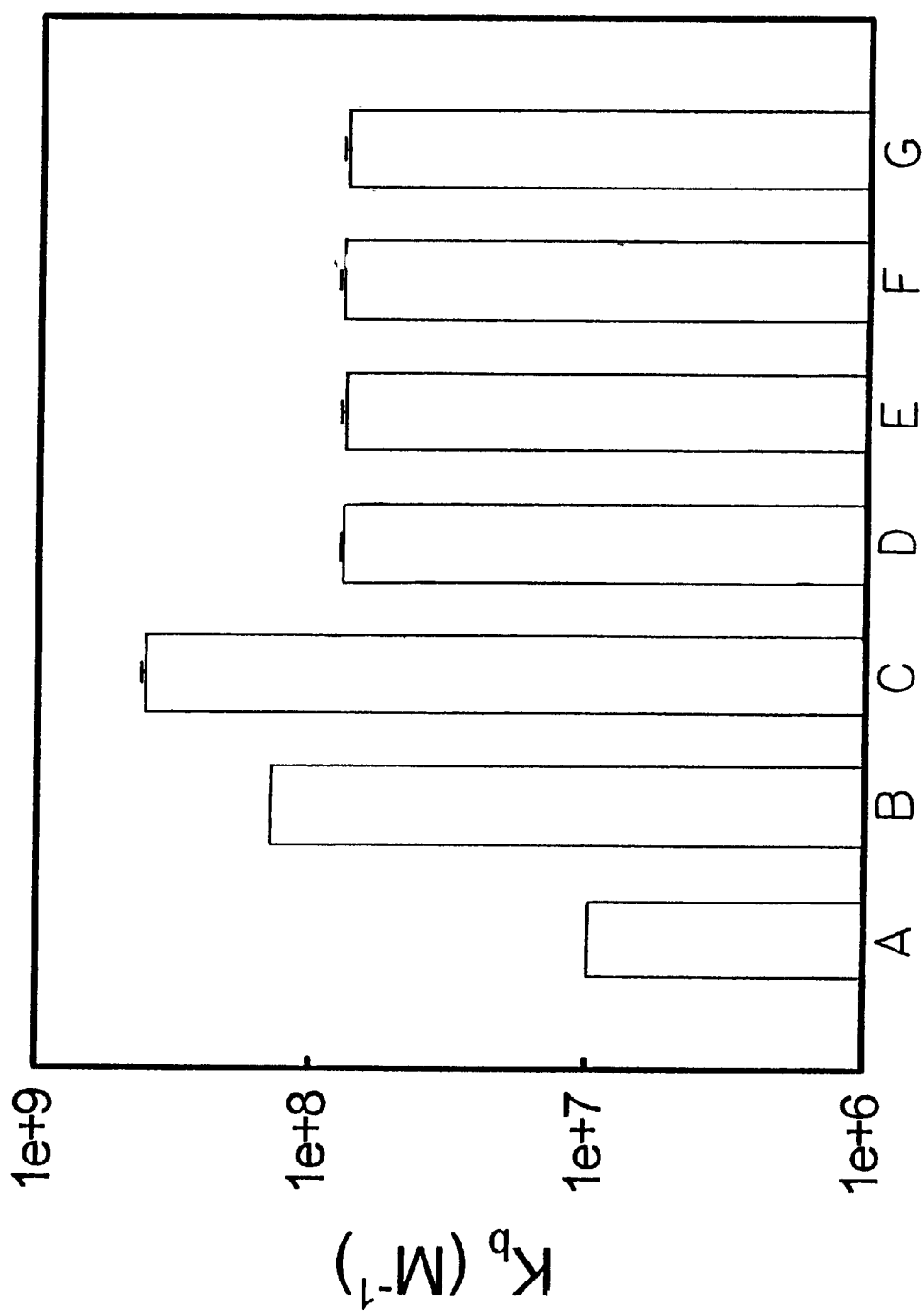
FIG. 13 shows a plot of the affinity constant of the chemical sensor, anti-dansyl antibodies, for its hapten, dansyl, when it is dissolved in buffer—(from *J. Mol. Biol.* 1970, 51, 573 (A) and *Biochemistry* 1981, 20, 4624 (B)); when the antibodies are dissolved in buffer (C); or when the anti-dansyl antibodies sequestered within a micro-well that uses a hybrid TMOS-based xerogel glass as the holding agent as a function of storage time within the xerogel-filled micro-well((D)—1 month of storage at ambient conditions; (E)—2 months of storage at ambient conditions;(F)—3 months of storage at ambient conditions; (G)—8 months of storage at ambient conditions).

In another illustration of this embodiment, the activity of an antibody was tested in the sol-gel-derived glass that was within a micro-well for various times of storage. FIG. 13 shows the affinity constant for a hapten-antibody complex, dansyl/anti-dansyl, sequestered in the sol-gel-derived glass according to the present invention as a function of storage time. Measurements are shown for the same micro-well sensor after storage for 1, 2, 3, and 8 months. Thus, this experiment illustrates that the antibody affinity is not significantly affected when it is sequestered within the xerogel glass for prolonged periods of time and array sensors based on antibodies are possible.

EXAMPLE 5

Figure 14:
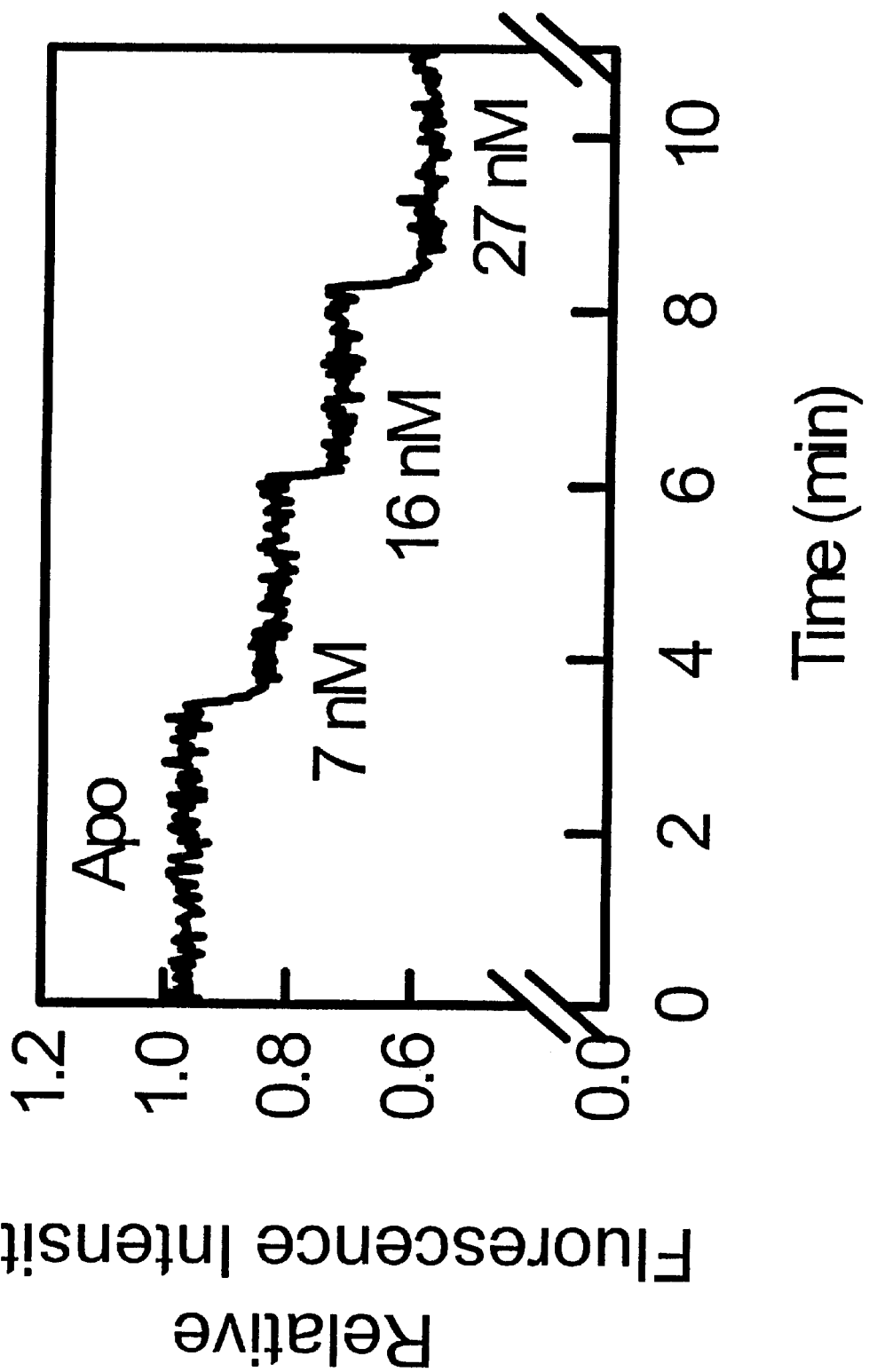
FIG. 14 shows the relative fluorescence intensity of electromagnetic radiation emitted by a sensor according to the present invention having fluorescein labeled calmodulin to selectively detect the presence of $Ca^{2+}$ in solution.

This embodiment illustrates that the device and method of the present invention can be used to detect and quantitate analytes. In the present experiment, a sensor element was attached to a molecule having a specific affinity for an analyte. For this experiment, calmodulin was site selectively labeled with a fluorescent molecule, fluorescein. The precise position of the fluorophore and the synthetic strategy used to prepare the fluorescein-labeled calmodulin (CaM-F) have been reported in A.N. Watkins and F.V. Bright, "Effects of Fluorescent Reporter Group Structure on the Dynamics Surrounding Cysteine-26 in Spinach Calmodulin: A Model Biorecognition Element," *Appl. Spectrosc.* 1998 52, 1447, which disclosure is incorporated herein by reference. The microwells on the face of an LED were filled with a TMOS-based sol-gel-processing solution that contained ~2 $\mu$M CaM-F and the fluorescence intensity from the micro-well was measured in the presence of various concentrations of free calcium ion. The relative fluorescence intensity as a function of time for CaM-F within a xerogel, within a micro-well as it is challenged with increasing concentrations of calcium ion is shown in FIG. 14. "Apo" refers to Apo-CaM which represents the state when no calcium ion is present to bind to CaM. At the three time points, the LED sensor was exposed to free calcium ion concentrations of 7 nM, 16 nM and 27 nM. As seen in FIG. 14, a rapid and measurable response is observed at each concentration illustrating that the device of the present invention can be used with protein-based recognition chemistries to selectively detect analytes.

Figures 15A, 15B:
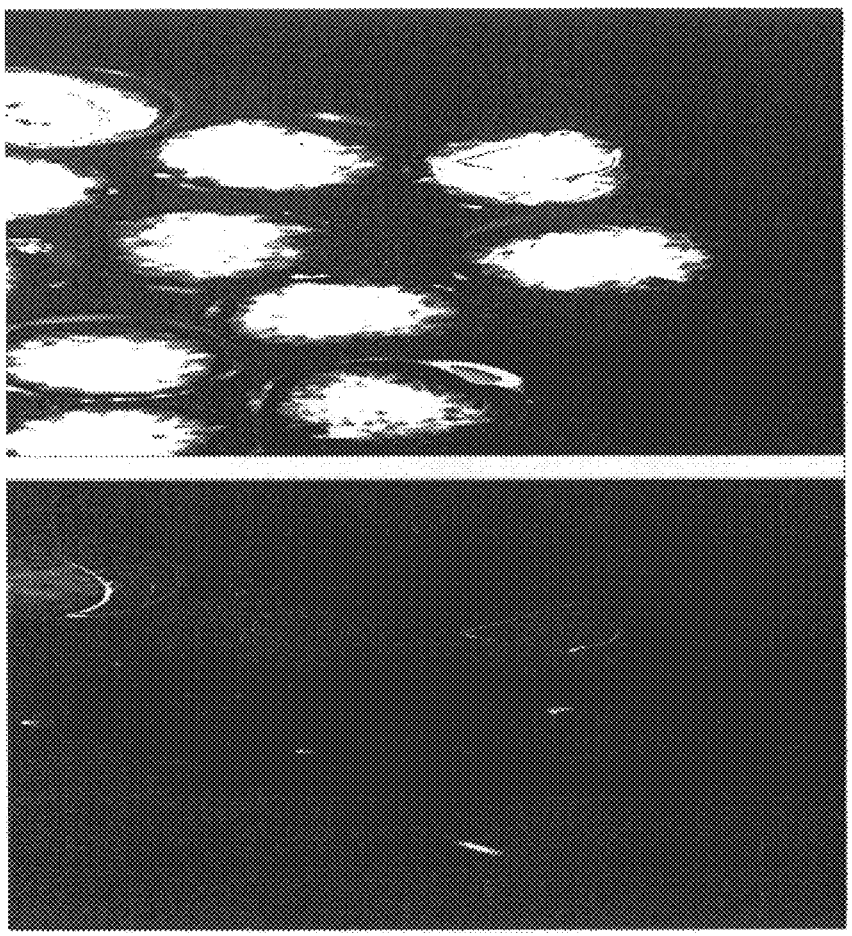
FIGS. 15, A and B show a fluorescence image of a micro-well array on the face of an LED having a fluorescein-labeled monoclonal antibody that is selective to benzo[a]pyrene in the absence (B) or presence (A) of 150 pM B[a]P to detect the presence of benzo[a]pyrene in solution. The signal to noise ration at 15 nM was 78.

In another illustration of this embodiment, an analyte was detected by using a sensor element attached to a monoclonal antibody specific for the analyte. A monoclonal antibody to benzo[a]pyrene (B[a]P) was labeled with fluorescein by methods well known in the art. FIG. 15 (panels A and B) shows an image of a micro-well array in the presence and absence of B[a]P dissolved in solution. In this particular reaction, the fluorescein residue fluorescence from its site(s) on the monoclonal anti-B[a]P antibody was enhanced by the binding of B[a]P to the antibody. Thus, the upper panel (A) in FIG. 15 represents fluorescence corresponding to a concentration of 150 pM B[a]P while the lower panel (B) represents fluorescence in the absence of B[a]P. The signal-to-noise for a 150 pM concentration of B[a]P was 78. Thus, this experiment illustrates that the device and method of the present invention can be used with antibody-based recognition chemistries, can operate in an array format, and offers detection limits in the low picomolar range.

Figure 16:
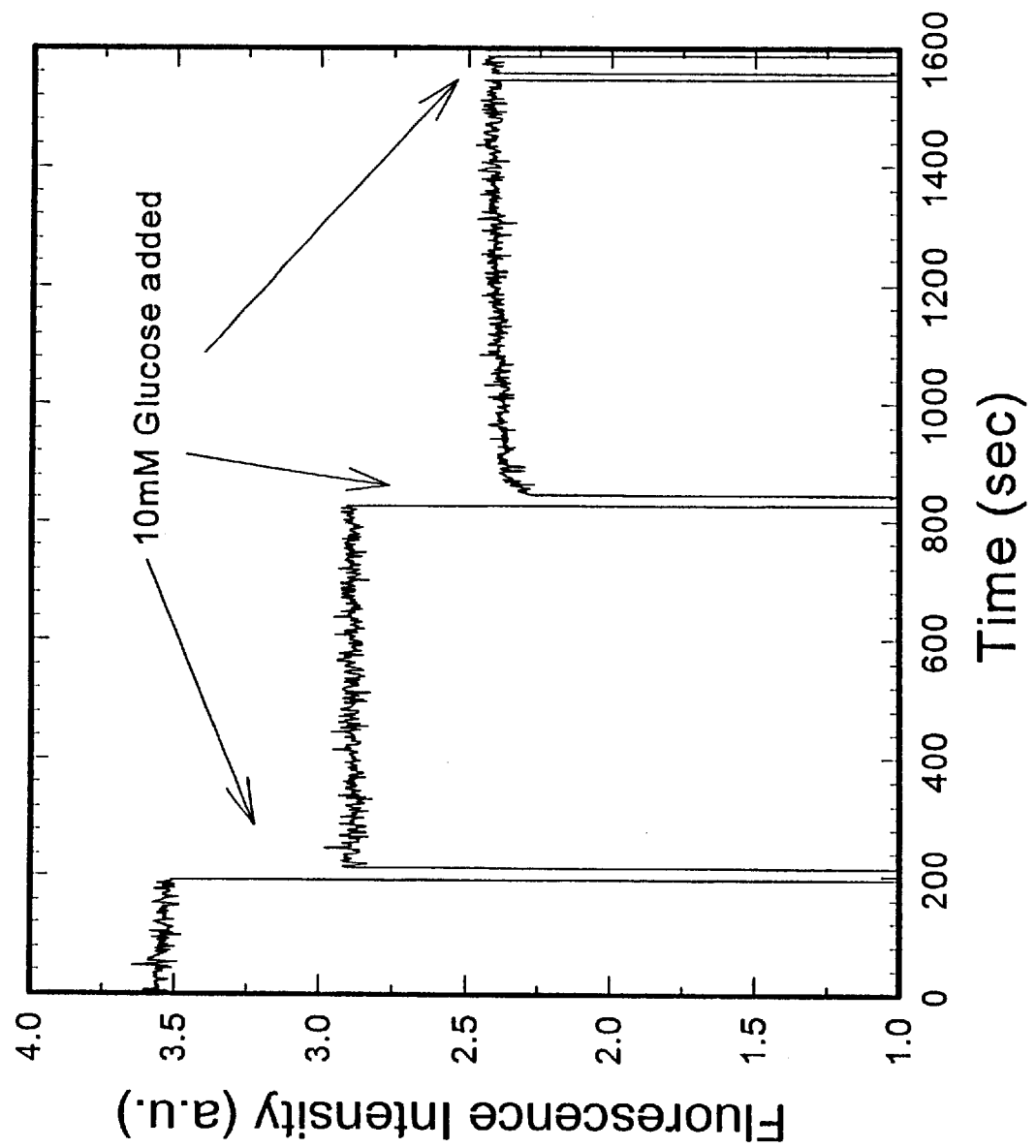
FIG. 16 is a plot of the intensity of fluorescence from a single micro-well located on the face of a LED having GOx as the chemical sensor, in the presence and absence of glucose.

In another illustration of this embodiment, the presence of glucose in a sample was detected by using glucose oxidase as the chemical sensor. In this particular format, the intrinsic fluorescence from the flavin adenine dinucleotide (FAD) residues that make-up the redox active site within GOx is monitored. FIG. 16 presents the fluorescence intensity response of the sensor in the absence of added glucose, after the addition of one 10 mM bolus of glucose and a second 10 mM bolus (20 mM total) of glucose. FIG. 16, thus, illustrates that the detecting device 10 can be used with enzyme-based recognition chemistries.

Figure 17:
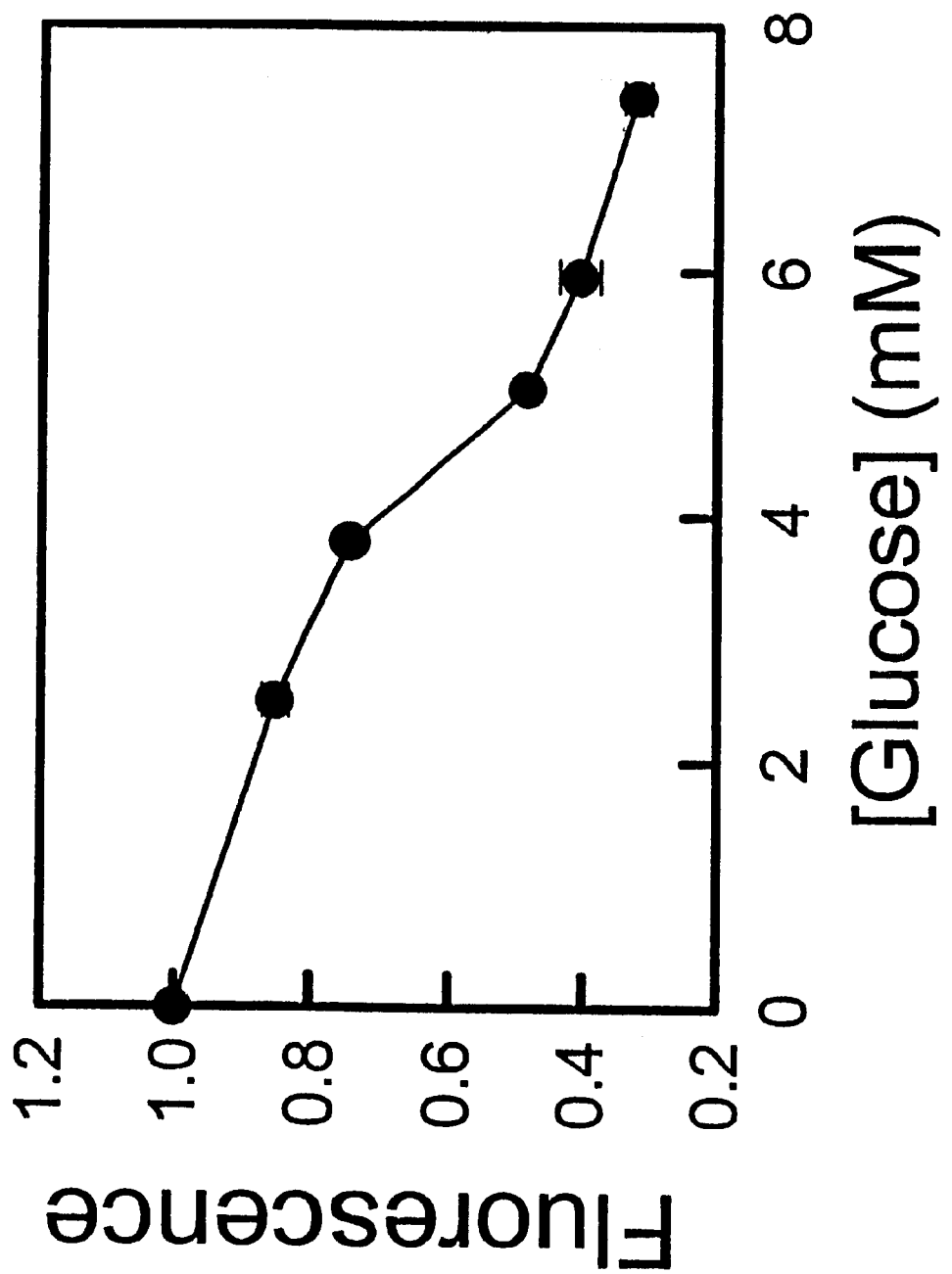
FIGS. 17–19 shows plots of fluorescence versus concentration of three different analytes, glucose, tyrosinase, and cholesterol, for three discrete micro-wells on the face of a single LED according to the present invention containing the chemical sensors GOx (FIG. 17), L-amino acid oxidase (L-AAO) (FIG. 18), and cholesterol oxidase (ChOX) (FIG. 19).
Figure 18:
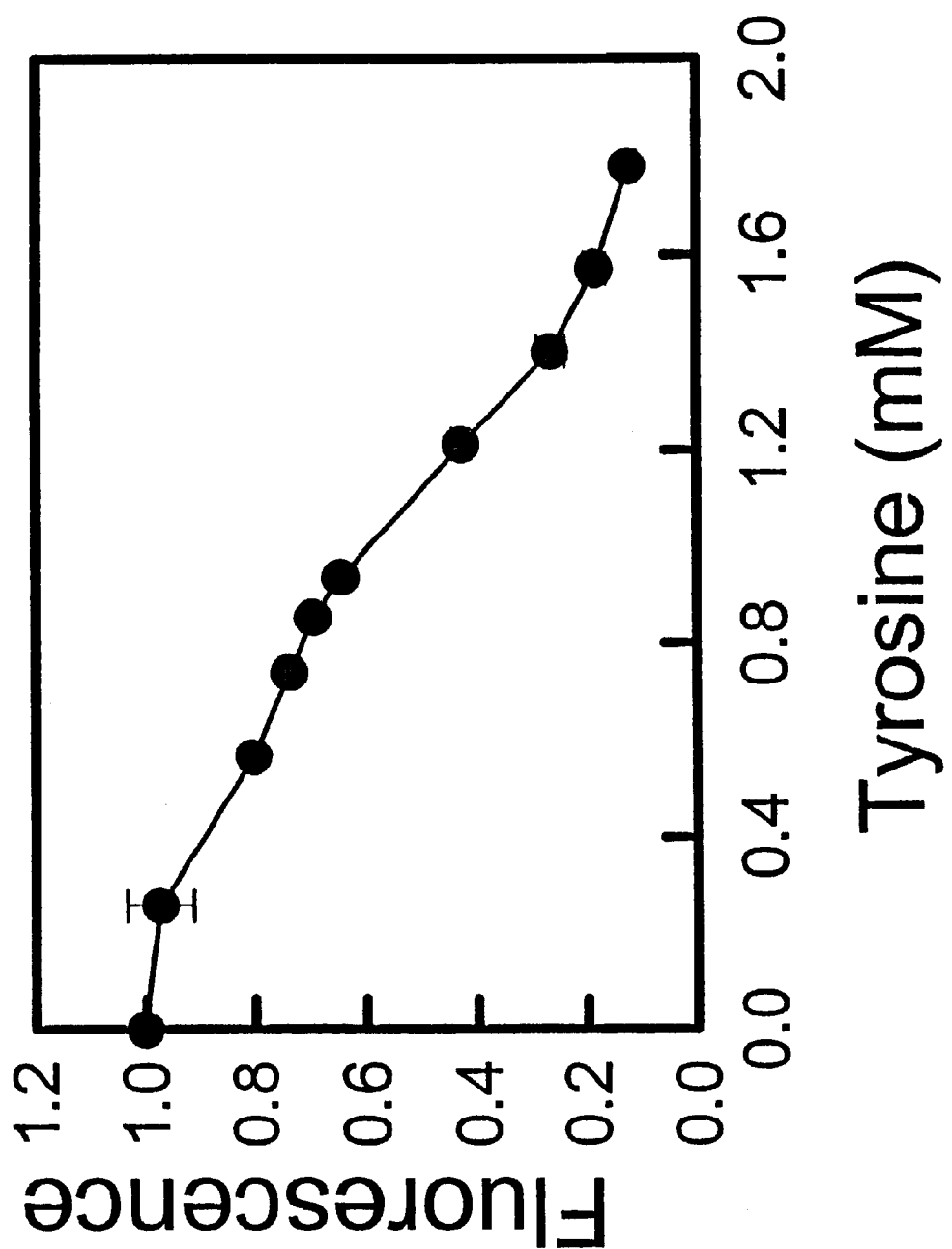
Figure 19:
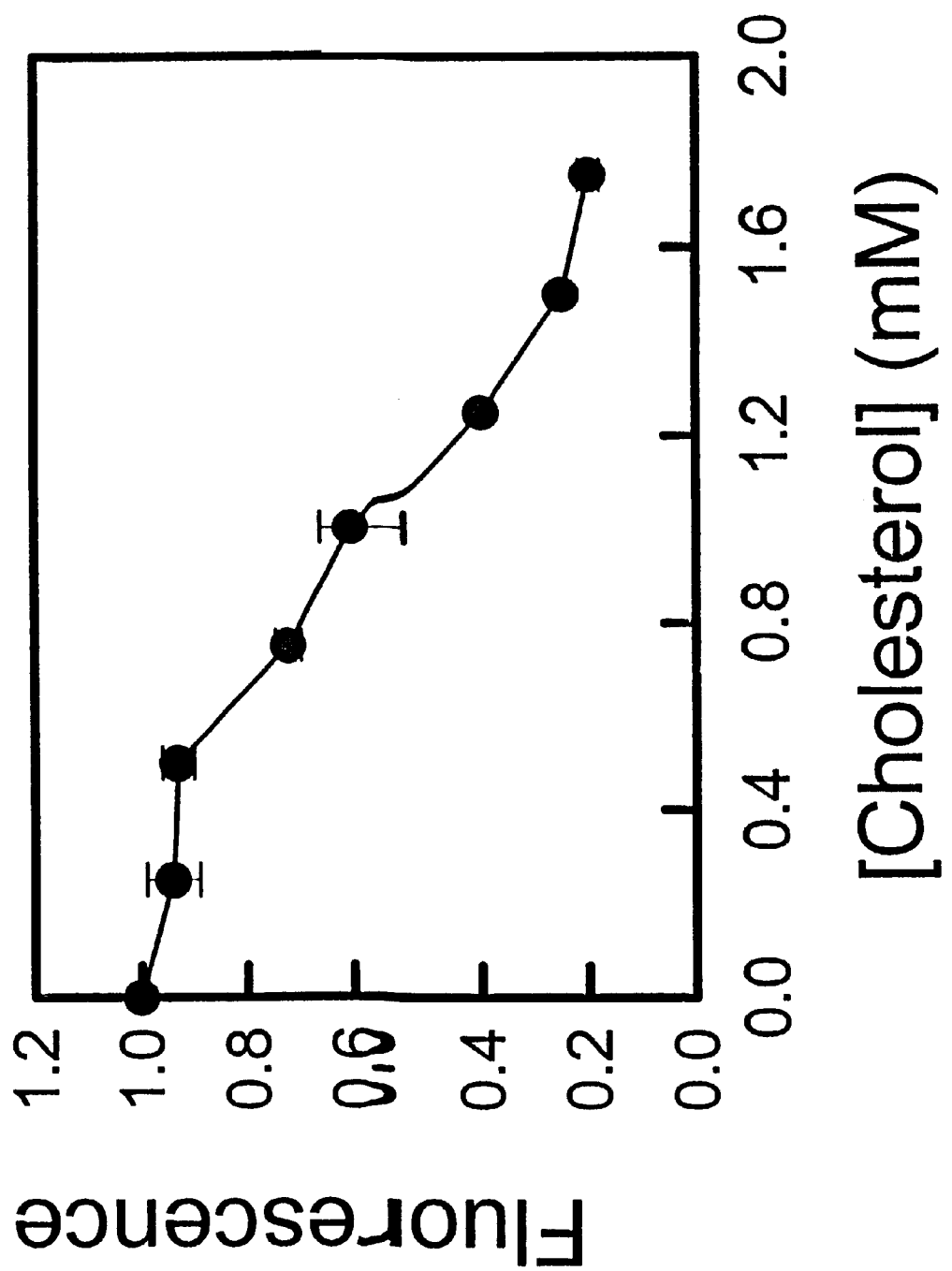

In another experiment, three different micro-wells located on the face of a single LED were filled with sol-gel-processed solutions that were individually doped with the sensors glucose oxidase (FIG. 17), L-amino acid oxidase (FIG. 18), and cholesterol oxidase (FIG. 19) respectively. By exposing these sensors to different concentrations of the appropriate substrates (i.e., glucose, tyrosinase and cholesterol), dose response curves shown in FIGS. 17–19 were generated. The flavin adenine dinucleotide (FAD) fluorescence was followed in this particular example so the detection wavelength was identical for each micro-well. FIGS. 17–19 again illustrates that the device and method of the present invention can be used with enzyme-based recognition chemistries. FIGS. 17–19 also shows the potential for calibration of the device as well as the use of an array of micro-wells in the simultaneous detection of multiple analytes in the same sample.

It should be apparent to those skilled in the art that the present invention accomplishes the intended objects described above. The present invention provides a detecting device wherein the chemical sensor can be placed in contact with the ER generator, making the device compact. Furthermore, the electromagnetic radiation used in the present invention is not reflected, filtered, or transmitted over a long distance prior to reaching the chemical sensor. In addition, the detecting device according to the present invention can be made relatively inexpensively and readily mass produced.

Although preferred embodiments of the present invention have been described and illustrated herein, the present invention is not limited to such preferred embodiments. Since various changes could be made without departing from the spirit and scope of the invention, it is intended that the foregoing description shall be interpreted as illustrative, and not interpreted in a limiting sense.

What is claimed is:

1. A device for detecting the presence of at least one analyte in a sample, comprising:
    an electromagnetic radiation generating source having a protective layer thereon, said protective layer having at least one well formed therein, wherein the bottom of the well does not reach the electromagnetic radiation generating source and wherein the protective layer is transparent or translucent; and
    a chemical sensor positioned in the well for reactive contact with the analyte in the sample, wherein the spectroscopic properties of the chemical sensor are modified in the presence of the analyte.

2. The device of claim 1, wherein the electromagnetic radiation generating source is a light emitting diode.

3. The device of claim 1, further comprising a receiving and interpreting system having electromagnetic radiation receiver to receive electromagnetic radiation emitted by the chemical sensor, and having an interpreter to interpret the received electromagnetic radiation.

4. The device of claim 3, wherein the receiver includes a filter for selectively passing electromagnetic radiation.

5. The device of claim 3, wherein the receiver includes a charge coupled device.

6. The device of claim 5, wherein the receiver includes a lens for focusing the electromagnetic radiation on the charge coupled device.

7. The device of claim 3, wherein the interpreter includes a computer.

8. The device of claim 1, further comprising a holding material for holding the chemical sensor in the well.

9. The device of claim 8, wherein the holding material is a sol-gel.

10. The device of claim 9, wherein the holding material is comprised of tetramethylorthosilane.

11. The device of claim 1, wherein the chemical sensor is comprised of a sensor element and an affinity molecule having a specific affinity for the analyte.

12. The device of claim 11, wherein the affinity molecule is an antibody to the analyte.

13. The device of claim 11, wherein the sensor element is selected from the group consisting of fluorophore, phosphore and chromophore.

* * * * *

UNITED STATES PATENT AND TRADEMARK OFFICE
CERTIFICATE OF CORRECTION

PATENT NO. : 6,492,182 B1
DATED : December 10, 2002
INVENTOR(S) : Bright et al.

It is certified that error appears in the above-identified patent and that said Letters Patent is hereby corrected as shown below:

Title page,
Item [*] Notice, delete the phrase "by 34 days" and insert -- by 0 days --.

Signed and Sealed this

Eleventh Day of October, 2005

JON W. DUDAS
*Director of the United States Patent and Trademark Office*